United States Patent [19]
Bickel et al.

[11] Patent Number: 5,364,873
[45] Date of Patent: Nov. 15, 1994

[54] PYRIDINE-2,4- AND DICARBOXYLIC ACID DERIVATIVES, THE USE THEREOF AND PHARMACEUTICAL COMPOSITION BASED ON THESE COMPOUNDS

[75] Inventors: Martin Bickel, Bad Homburg; Dietrich Brocks, Wiesbaden; Harald Burghard, Schmitten; Volkmar Günzler, Marburg-Cappel; Stephan Henke, Bad Soden am Taunus, all of Germany

[73] Assignee: Hoechst Aktiengesellschaft, Frankfurt am Main, Germany

[21] Appl. No.: 21,139

[22] Filed: Apr. 1, 1993

Related U.S. Application Data

[60] Division of Ser. No. 932,738, Aug. 25, 1992, Pat. No. 5,238,948, which is a continuation of Ser. No. 690,315, Apr. 25, 1991, abandoned, which is a continuation of Ser. No. 555,675, Jul. 19, 1990, abandoned, which is a continuation of Ser. No. 153,086, Feb. 8, 1988, abandoned.

[30] Foreign Application Priority Data

Feb. 10, 1987 [DE] Germany .............. 3703963

[51] Int. Cl.⁵ ............... A61K 31/44; C07D 213/81
[52] U.S. Cl. .................... 514/354; 514/335; 514/336; 514/340; 514/342; 546/261; 546/262; 546/276; 546/278; 546/279; 546/280; 546/284
[58] Field of Search ............ 546/323; 514/354

[56] References Cited

U.S. PATENT DOCUMENTS

| | | | |
|---|---|---|---|
| 2,654,759 | 10/1953 | Suter et al. | 546/316 |
| 2,852,519 | 9/1958 | Kurse | 546/321 |
| 3,781,286 | 12/1973 | Minisci et al. | 546/169 |
| 4,067,975 | 1/1978 | Yu et al. | 514/352 |
| 4,141,977 | 2/1979 | Yu et al. | 546/318 |
| 4,775,763 | 10/1988 | Dalton et al. | 546/286 |
| 4,785,111 | 11/1988 | Toda | 546/316 |

FOREIGN PATENT DOCUMENTS

| | | |
|---|---|---|
| 0057797 | 8/1982 | European Pat. Off. . |
| 0198202 | 10/1986 | European Pat. Off. . |
| 0278908 | 8/1988 | European Pat. Off. . |
| 2803592 | 3/1979 | Germany . |
| 3432094 | 3/1986 | Germany . |
| 85/6646 | 8/1985 | South Africa . |

OTHER PUBLICATIONS

Tani, Yakugaku Zasshi vol. 80, pp. 1418–1424 (1960): Chem. Abstracts, vol. 55, 6477i (1961).
Heh et al., Inorganic Chem., vol. 17(11), pp. 3138–3142 (1978).
Müller et al., "Reversible Inhibition of C1Q Release from Guinea Pig Macrophages by 2,2′-Dipyridyl," FEBS Letters, 90:218–222 (1978).
Majamaa et al., "The 2-Oxoglutarate Binding Site of Prolyl 4-Hydroxylase," Eur. J. Biochem., 138:239–245 (1984).
Gunzler et al., "Inhibition of Prolyl–4–Hydroxylase by Structure Analogues of 2-Oxoglutarate," Collagen and Rel. Research, 3:71 (1983).

(List continued on next page.)

*Primary Examiner*—Bernard Dentz
*Attorney, Agent, or Firm*—Finnegan, Henderson, Farabow, Garrett & Dunner

[57] ABSTRACT

The invention relates to pyridine-2,4- and -2,5-dicarboxylic acid derivatives of the formula I

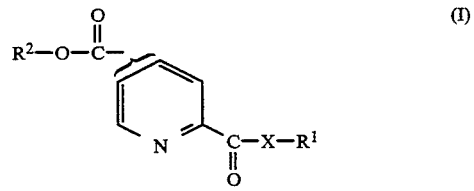

in which $R^1$, $R^2$ and X have the meanings given, a process for the preparation of these compounds and their use, in particular in medicaments for influencing the metabolism of collagen and collagen-like substances or the biosynthesis of $C1_q$.

12 Claims, No Drawings

OTHER PUBLICATIONS

Rouiller, The Liver, vol. II, Acadmeic Press, New York (1964), pp. 335–476.

Delarge, "Contribution a la synthese des acides thiolpyridine-carboxyliques," Pharm. Acta Helv., 44:637–643 (1969).

J. Org. Chem., 39:1158 (1974).

Müller et al., "Influence of the Posttranslational Hydroxylation Step on the Secretion of C1q, a Subcomponent of the First Component of Complement, by Macrophages," Immunobiology, 155:47 (1978).

Houben-Weyl, Methoden der Organischen Chemie, vol. XV/2 (1974), pp. 103–111.

Organikum, Organisch Chemisches Grundpraktikum (15th ed. 1976), pp. 595 et seq.

Houben-Weyl, vol. IV/1C (1980), pp. 381–382.

Organikum, Organisch Chemisches Grundpraktikum (15th ed. 1976), p. 527.

Houben-Weyl, Methoden der Organischen Chemie, vol. XV/2 (1974), pp. 169–183.

A. Hubbuch, Schutzgruppen in der Peptidsynthese (Teil 1): Schutzgruppentaktick, Amino-und Carboxyl-Schutzgruppen, Kontakte, Mar. 1979, pp. 15 & 19 et seq.

Houben-Weyl, Methoden der Organischen Chemie (Methods of Organic Chemistry) vol. E5, 4th Ed. (1985), pp. 496–504.

Organikum, Organisch Chemisches Grundpraktikum, VEB Deutscher Verlag der Wissenschaften, (15th ed. 1976), pp. 821–822.

Organikum, Organisch Chemisches Grundpraktikum, VEB Deutscher Verlag der Wissenschaften, (15th ed. 1976), pp. 255–256.

Chemical Abst. (of Meyer, Rec. Trav. Chim. 44:323–328 (1925), vol. 19), (1925), pp. 2953–2954.

Chemical Abst., 58:2431e (1963).

Chemical Abst., 87:90773c (1977).

Elke Langhals et al., "Eine einfache neue Synthese der Fusarinsäure und anderer 5-Alkyl-2-pyridincarbonsäuren," Liebigs Ann. Chem., No. 5, pp. 930–949 (1982).

Wada et al., "Bisisoquinolines", Chemical Abstracts, 80:108395y (1974).

G. J. Atwell and B. F. Cain, "Potential Antitumor Agents, V. Bisquaternary Salts," J. Med. Chem., 10:706–713 (1966).

Rekker et al., "The Hydrophobic Fragmental Constant: an Extension to a 1000 Data Point Set," Eur. J. Med. Chem.-Chimica Therapeutica, 14:479–488 (1979).

Talma et al., "Reductions of Activated Carbonyl Compounds with Chiral Bridged 1,4-Dihydropyridines. An Investigation of Scope and Structural Effects," J. Amer. Chem. Soc., 107:3981–3997 (1985).

Samejima, "Solubilizing Agents," Chemical Abstracts, 55:10439–10440 (1961).

Peterson, "Nitrogen-Substituted Derivatives of 2,5-Pyridinedicarboxylic Acid," Chemical Abstracts, 54:19674–19675 (1960).

Thunus et al., "Preparation Des Monesters Des Acides Pyridine-Dicarboxyliques," Journal De Pharmacie De Belgique, pp. 3-21 (1968).

Dewar et al., "Effect of Structure on the Stability of Nematic Mesophases," J. Amer. Chem. Soc., 97 (23), pp. 733–741.

Wolfensberger et al., "Identification of Quinolinic Acid in Rat and Human Brain Tissue," Neuroscience Letters, 41:247–252 (1983).

Prostakov et al., "Substituted Pyridines. Amides and Hydrazides of Pyridinecarboxylic Acids," Chem. Absts., 64:3464–3465 (1966).

McMillan et al., "Hexamethylene-1,6-bis-t-amines in Which Part of the Six Carbon Chain is also Part of a Six-membered Ring," J. American Chemical Abstracts, 78:4077–4081 (1956).

Ried et al., "Hydrogenolyse N-Substituierter Amide Von Pyridin-Dicarbon-säuren und -Tricarbonsäuren," Ann. 666, Univ. Frankfurt a.M., Ger., pp. 148–155 (1963).

Ried et al., "Hydrogenolysis of N-Substituted Amides of Pyridinedi-and -tricarboxylic acids," Chem. Absts., 37-Heterocyclic Compounds, col. 12754 (1963).

Queguiner et al., "Chimie Organique-Essais de preparation des dialdehydes de la pyridine," Acad. Sc. Paris, t 258, Group 8, pp. 5903–5906 (1964).

PYRIDINE-2,4- AND DICARBOXYLIC ACID DERIVATIVES, THE USE THEREOF AND PHARMACEUTICAL COMPOSITION BASED ON THESE COMPOUNDS

This is a division of application Ser. No. 07/932,738, filed Aug. 25, 1992, now U.S. Pat. No. 5,238,948, which is a continuation of U.S. Ser. No. 07/690,315, filed Apr. 25, 1991, abandoned, which is a continuation of U.S. Ser. No. 07/555,675, filed Jul. 19, 1990, abandoned, which is a continuation of U.S. Ser. No. 07/153,086, filed Feb. 8, 1988, abandoned.

Compounds which inhibit proline hydroxylase and lysine hydroxylase effect very selective inhibition of collagen biosynthesis by influencing collagen-specific hydroxylation reactions. In the course of these, protein-bonded proline or lysine is hydrolyzed by the enzymes proline hydroxylase and lysine hydroxylase. If this reaction is suppressed by inhibitors, a hypo-hydroxylated collagen molecule which is not capable of functioning and is released by the cell into the extracellular space in only a small amount is formed, The hypo-hydroxylated collagen also cannot be incorporated into the collagen matrix and is very readily degraded proteolytically. As a consequence of these effects, the total amount of extracellularly deposited collagen is reduced.

It is known that inhibition of proline hydroxylase by known inhibitors, such as $\alpha,\alpha'$-dipyridyl, leads to an inhibition of the $C1_q$-biosynthesis of macrophages (W. Müller et al., FEBS Lett. 90 (1978), 218; and Immunbiology 155 (1978) 47). There is thus a loss of the classical route of complement activation. Inhibitors of proline hydroxylase therefore also act as immunosuppressants, for example in immunity complex diseases.

It is known that proline hydroxylase is inhibited effectively by pyridine-2,4- and -2,5-dicarboxylic acid (K. Mayama et al., Eur. J. Biochem. 138 (1984) 239–245). However, these compounds are active as inhibitors in the cell culture only in very high concentrations (V. Gunsler et at. Collagen and Rel. Research 3, 71 1983).

DE-A-3,432,094 describes pyridine-2,4- and -2,5-dicarboxylic acid diesters with 1–6 carbon atoms in the ester alkyl part as medicaments for inhibiting proline hydroxylase and lysine hydroxylase.

However, these lower alkyl diesters have the disadvantage that they are split too rapidly in the organism to give the acids and do not arrive at their site of action in the cell in a sufficiently high concentration, and therefore are not particularly suitable for possible administration as medicaments.

Surprisingly, it has now been found that the mixed ester/amides of pyridine-2,4- and -2,5-dicarboxylic acid and likewise the higher alkylated diesters are excellent inhibitors of collagen biosynthesis in the animal model.

The actual active compound, the pyridine-2,4- or -2,5-dicarboxylic acid, is first formed in the cell by hydrolysis of the esters or ester/amides. On the basis of their higher lipophilicity and the fact that, surprisingly, they are hydrolyzed only very slowly during transportation, the esters and ester/amides can be transported into the cells. Only here is the actual active compound, the pyridine-2,4- or -2,5-dicarboxylic acid, released.

The invention thus relates to:

1. Pyridine-2,4- and -2,5-dicarboxylic acid derivatives of the formula I

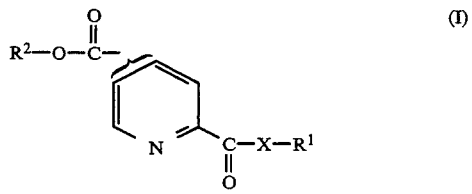

in which $R^1$ denotes branched or unbranched $C_1$–$C_{12}$-alkyl which is optionally monosubstituted or, in the case of the $C_2$–$C_{12}$-alkyl radicals, also polysubstituted by halogen, hydroxyl, cyano, carboxyl, alkoxy, alkoxycarbonyl, alkylcarbonyloxy or alkyl- or dialkylamino, the alkyl rad meals containing 1–4 carbon atoms and, in the case of the $C_3$- and $C_4$-alkyl radicals, it also being possible for them to be branched, phenyl, which is in turn optionally mono-, di- or trisubstituted by halogan, nitro, $C_1$–$C_4$-alkyl or $C_1$–$C_4$-alkoxy, it also being possible, in the case of polysubstitution, for the substituents to differ independently of one another and it also being possible, in the case of the $C_3$- and $C_4$-alkyl radicals, for these to be branched, or $R^1$ denotes saturated $C_5$–$C_7$-cycloalkyl, which is optionally benzo-fused, or $R^1$ denotes aryl or heteroaryl, which in turn is optionally mono-, di- or trisubstituted by halogen, $C_1$–$C_4$-alkyl or $C_1$–$C_4$-alkoxy, it also being possible, in the case of polysubstitution, for the substituents to differ independently of one another and it also being possible, in the case of the $C_3$- and $C_4$-alkyl radicals, for these to be branched, or $R^1$ denotes 2-oxo-1,3-dioxolylmethyl, which is optionally also methyl-substituted, or $R^1$, if X is nitrogen, denotes hydrogen, and $R^2$ independently of $R^1$ denotes hydrogen or $R^1$, it also being possible for $R^2$ to be identical to $R^1$, and X denotes oxygen or $R^3$-substituted nitrogen, in which $R^3$ is hydrogen or $C_1$–$C_6$-alkyl or, together with $R^1$ optionally forms a heterocyclic saturated 5-, 6- or 7-ring, it also being possible for the heterocyclic ring to include a second nitrogen atom and it being possible for the heterocyclic ring in turn to be substituted by phenyl or phenyl-$C_1$–$C_3$-alkyl, and physiologically tolerated salts thereof for use as medicaments, excluding the compounds in which X denotes oxygen and $R^1$ and $R^2$ at the same time denote unsubstituted $C_1$–$C_6$-alkyl.

The invention particularly relates to pyridine-2,4- and -2,5-dicarboxylic acid derivatives according to formula I, in which $R^1$ denotes branched or unbranched $C_1$–$C_4$-alkyl which is optionally monosubstituted or, in the case of the $C_3$- and $C_4$-alkyl radicals, also polysubstituted by $C_1$–$C_3$-alkoxy and/or $C_1$–$C_3$-alkoxycarbonyl, it also being possible for the $C_3$-alkyl radicals to be branched, and/or phenyl, $R^1$ denotes $C_5$- or $C_6$-cycloalkyl, which is optionally benzo-fused, or $R^1$ denotes phenyl, which is optionally mono-, di- or trisubstituted by nitro, or $R^1$ denotes 2-, 3- or 4-pyridyl, naphthyl, 2- or 3-thienyl, pyrazolyl, imidazolyl or thiazolyl, or $R^1$ denotes 5-methyl-2-oxo-1,3-dioxol-4-yl-methyl and $R^2$ independently of $R^1$ denotes hydrogen or $R^1$, it also being possible for $R^2$ to be identical to $R^1$, and X denotes oxygen or $R^3$-substituted nitrogen, in which $R^3$ is hydrogen or $C_1$–$C_3$-alkyl or, together with $R^1$, optionally forms a heterocyclic saturated 6-ring, it also being possible for the heterocyclic 6-ring to include a second nitrogen atom and to be substituted in turn by phenyl or phenyl-$C_1$–$C_3$-alkyl, and physiologically tolerated salts thereof, for use as medicaments, excluding the compounds in which X denotes oxygen and $R^1$ and $R^2$ at the same time are unsubstituted $C_1$–$C_4$-alkyl, The invention also relates to pyridine-2,4- and -2,5-dicarboxylic acid derivatives of the formula I'

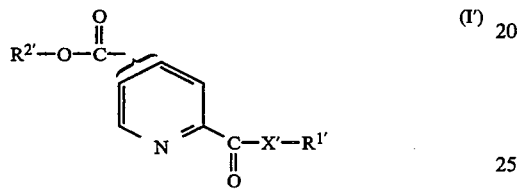

in which $R^{1'}$ denotes branched or unbranched $C_1$–$C_{12}$-alkyl which is optionally monosubstituted or, in the case of $C_2$–$C_{12}$-alkyl, also polysubstituted by halogen, hydroxyl, cyano, carboxyl, alkoxy, alkoxycarbonyl, alkylcarbonyloxy or alkyl- or dialkylamino, the alkyl radicals containing 1–4 carbon atoms and it also being possible, in the case of the $C_3$- and $C_4$-alkyl radicals, for these to be branched, phenyl, which is in turn optionally mono-, di- or trisubstituted by halogen, $C_1$–$C_4$-alkoxy or $C_1$–$C_4$-alkyl, it also being possible for the $C_3$- and $C_4$-alkyl radicals mentioned to be branched and it also being possible, in the case of polysubstitution, for the substituents to differ independently of one another, or $R^{1'}$ denotes saturated $C_5$–$C_7$-cycloalkyl, which is optionally benzo-fused, or $R^{1'}$ denotes aryl or heteroaryl, which is in turn optionally mono-, di- or trisubstituted by halogen, nitro, $C_1$–$C_4$-alkyl or $C_1$–$C_4$-alkoxy, it also being possible, in the case of polysubstitution, for the substituents to differ independently of one another and it also being possible, in the case of the $C_3$- and $C_4$-alkyl radicals, for these to be branched, or $R^{1'}$ denotes 2-oxo-1,3-dioxolylmethyl, which is optionally methyl-substituted, or $R^{1'}$, if X' is nitrogen, denotes hydrogen, and $R^{2'}$ independently of $R^{1'}$ denotes hydrogen or $R^{1'}$, it also being possible for $R^{2'}$ to be identical to $R^{1'}$, and X' denotes oxygen or $R^{3'}$-substituted nitrogen, in which $R^{3'}$ is hydrogen or $C_1$–$C_6$-alkyl or, together with $R^{1'}$, optionally forms a heterocyclic, saturated 5-, 6- or 7-ring, it also being possible for the heterocyclic ring to include a second nitrogen atom and it being possible for the heterocyclic ring in turn to be substituted by phenyl or phenyl-$C_1$–$C_3$-alkyl, and physiologically tolerated salts thereof, excluding the compounds in which X' denotes oxygen and $R^{1'}$ and $R^{2'}$ at the same time are unsubstituted $C_1$–$C_{12}$-alkyl or methyl or ethyl which is substituted by chlorine, hydroxyl or phenyl.

Preferred pyridine-2,4- and -2,5-dicarboxylic acid derivatives according to formula I' are those in which $R^{1'}$ denotes branched or unbranched $C_1$–$C_4$-alkyl, which is optionally monosubstituted or, in the case of the $C_2$–$C_4$-alkyl radicals, also polysubstituted by alkoxy or alkoxycarbonyl, the alkyl radicals containing 1–3 carbon atoms and it also being possible, in the case of the $C_3$-alkyl compounds, for these to be branched, or phenyl or $R^{1'}$ denotes cyclopentyl or cyclohexyl, which are optionally benzo-fused, or $R'$ denotes phenyl, which is optionally substituted by 1, 2 or 3 nitro groups, or naphthyl, or $R^{1'}$ denotes 3- or 4-pyridyl, 3-thienyl, pyrazolyl, imidazolyl or thiazolyl, or $R^{1'}$ denotes ethyl-2-oxo-1,3-dioxol-4-yl-methyl and $R^{2'}$ independently of $R^{1'}$ denotes hydrogen or $R^{1'}$, it also being possible for $R^{2'}$ to be identical to $R^{1'}$, and X' denotes oxygen or $R^{3'}$-substituted nitrogen, in which $R^{3'}$ is hydrogen or $C_1$–$C_3$-alkyl or, together with $R^{1'}$, optionally forms a heterocyclic, saturated 6-ring, it also being possible for the heterocyclic 6-ring to include a second nitrogen atom and in turn to be substituted by phenyl or phenyl-$C_1$–$C_3$-alkyl, and physiologically tolerated salts thereof, excluding the compounds in which X' denotes oxygen and $R^{1'}$ and $R^{2'}$ at the same time are unsubstituted $C_1$–$C_4$-alkyl or phenyl-substituted methyl or ethyl.

Particularly preferred pyridine-2,4- and -2,5-dicarboxylic acid derivatives of the formula I' are those in which $R^{1'}$ is branched or unbranched $C_1$–$C_4$-alkyl, which is substituted by alkoxycarbonyl, the alkyl radicals containing 1–3 carbon atoms and it also being possible, in the case of the $C_3$-alkyl radicals, for these to be branched, and $R^{2'}$ independently of $R^{1'}$ denotes hydrogen or $R^{1'}$, it also being possible for $R^{2'}$ to be identical to $R^{1'}$, and X' denotes oxygen, and physiologically tolerated salts thereof.

These compounds have, inter alia, a particular activity on oral administration, as do the especially preferred pyridine-2,4- and -2,5-dicarboxylic acid derivatives of formula I' in which $R^{1'}$ and $R^{2'}$ are 1-isopropoxycarbonylethyl groups and X' denotes oxygen (such as, for example, bis(1-isopropoxycarbonylethyl) pyridine-2,5-dicarboxylate (Example 3 ) or bis(1-isopropoxycarbonylethyl) pyridine-2,4-dicarboxylate (Example 30), and physiologically tolerated salts thereof.

By halogen there are understood fluorine, chlorine, bromine and iodine, by aryl there are understood phenyl and naphthyl and by heteroaryl there are understood 5- and 6-membered aromatic rings which contain 1, 2 or 3 nitrogen and/or oxygen and/or sulfur atoms and can optionally also be benzo-fused; the heteroaryl radicals are, in particular, pyridyl, pyridazyl, pyrimidyl, pyrazyl, 1,3,5-triazyl, pyrolyl, pyrazolyl, imidazolyl, triazolyl, thienyl, oxazolyl and thiazolyl radicals and where appropriate benzo-fused compounds thereof, "Polysubstituted" above and below means that at least 2 and at most all of the hydrogen atoms present in the alkyl radicals are replaced by the substituents mentioned, It is preferably a matter here of one substituent per methyl or methylene group, In the case of polysubstitution, the substituents can also differ independently of one another, The invention furthermore relates to a process for the preparation of compounds of the formula I', which comprises a) reacting a compound of the formula II

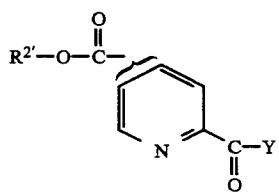
(II)

with a compound of the formula III

HX'—R¹'  (III)

in which $R^{1'}$, $R^{2'}$ and $X'$ have the meanings given in the case of formula I' and Y is halogen or hydroxyl, or b) reacting a compound of the formula IV

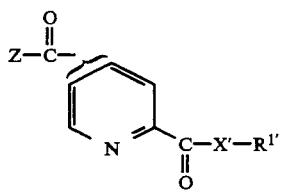
(IV)

with a compound of the formula V

HO—R²'  (V)

in which $R^{1'}$, $R^{2'}$ and $X'$ have the meanings given in the case of formula I' and Z is halogen, or c) reacting a compound of the formula VI

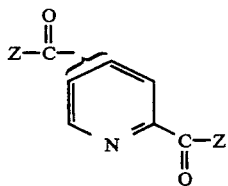
(VI)

with an alcohol HO—R²' or an alcohol of the formula VII

HO—R¹'  (VII)

wherein $R^{1'}$ and $R^{2'}$ have the meanings given in the case of formula I' and Z is halogen, or d) reacting an alkali metal salt of pyridine-2,4- or -2,5-dicarboxylic acid with a halide of the formula VIII

R¹'—Z  (VIII)

wherein $R^{1'}$ has the meanings given in the case of formula I' and Z is halogen,
and, if appropriate, converting the reaction products into their physiologically tolerated salts, The preparation of compounds according to formula I and the preparation of the starting substances required for this—where they are not commercially available—are described in more detail below.

The compounds according to the invention are most easily prepared by mixing the two components, the pyridine derivative according to formula (II), (IV) or (VI) and the amine or alcohol according to formula (III), (V) or (VII), in equimolar amounts or with up to an approximately 5-fold excess of III, V or VII, and reacting them at temperatures between −30° and 150° C., preferably at 20° to 100° C., until the reaction has ended. The end of the reaction can be determined by means of thin layer chromatography (TLC control). One variant of this process comprises carrying out the reaction in a suitable solvent, such as diethyl ether, dimethoxyethane or tetrahydrofuran, chlorinated hydrocarbons, such as methylene chloride, chloroform or tri- or tetrachloroethylene, benzene, toluene or polar solvents, such as dimethylformamide, acetone or dimethyl sulfoxide. An excess of amine/alcohol according to formula (III), (V) or (VII), which can be up to 5 times the amount, can also be used here. The reaction temperatures here are between room temperature and the boiling point of the solvent, temperatures in the range from room temperature to 130° C. being particularly preferred.

If appropriate, the reaction can also be carried out in the presence of bases. Possible additional bases are inorganic acid-trapping agents, such as carbonates or bicarbonates, for example sodium carbonate, potassium carbonate, sodium bicarbonate or potassium bicarbonate, or organic acid-trapping agents, such as tertiary amines, such as triethylamine, tributylamine or ethyl diisopropylamine, or heterocyclic amines, such as N-alkylmorpholines, pyridine, quinoline or dialkylanilines.

The reaction of the compounds according to formula (II) with alcohols according to formula (III) (X'=O) is preferably carried out with the addition of a dehydrating agent, such as a dialkylcarbodiimide, the alkyl radicals containing 1 to 8 carbon atoms and it also being possible, in the case of the $C_3$-$C_8$-compounds, for these to be branched or cyclic; dicyclohexylcarbodiimide is preferably used. A corresponding method is described in Houben-Weyl, Volume XV/2, pages 103-111, Methoden der Organischen Chemie (Methods of Organic Chemistry), 4th edition, Georg Thieme Verlag, Stuttgart, 1974.

If appropriate, the products can be worked up, for example by extraction or by chromatography, for example over silica get. The isolated products can be recrystallized and if appropriate reacted with a suitable acid to give a physiologically tolerated salt. Examples of possible suitable acids are: mineral acids, such as hydrochloric and hydrobromic acid, as well as sulfuric, phosphoric, nitric or perchloric acid, or organic acids, such as formic, acetic, propionic, succinic, glycolic, lactic, malic, tartaric, citric, maleic, fumaric, phenylacetic, benzoic, methanesulfonic, toluenesulfonic, oxalic, 3-aminobenzoic, naphthalene-1,5-disulfonic or ascorbic acid, The starting compounds of the formula (III), (V) and (VII), where they are not commercially available, can be synthesized in a simple manner (for example Organikum, Organisch Chemisches Grundpraktikum (Basic Practical Organic Chemistry), 15th edition, VEB Deutscher Verlag der Wissenschaften, 1976; a review of the various possibilities is to be found in the method register; Alcohols: page 821, Amines: page 822), The starting compounds of the formula (II) are obtained, for example, by converting pyridine-2,4- or -2,5-dicarboxylic acid into the corresponding pyridine-2,4- or -2,5-dicarboxylic acid halide (VI), preferably the chloride (by processes which are known from the literature, for example Organikum, Organisch Chemisches Grundpraktikum (Basic Practical Organic Chemistry), 15th edition, VEB Deutscher Verlag der Wissenschaften, 1976, page 595 et seq.), which is then reacted with an alcohol of the formula $R^{2'}$—OH (V) to give the corresponding 2,4- or 2,5-diester. Selective hydrolysis of the ester in the 2-position of the pyridine derivative (for example by a copper complex, see Pharm. Acta Helv. 44 1969, page 637) or partial alkaline hydrolysis (see J. Org. Chem. 39 (8) 1974, page 1158) gives the pyridine-4- or -5-carboxylic acid ester-2-carboxylic acid, which is either used directly (II, Y=OH) or can be converted into the acid halide (II, Y=Cl, Br or I), preferably the acid chloride.

The starting compounds of the formula (IV) can be synthesized, for example, as follows:

Reaction of the pyridine-2,4- or -2,5-dicarboxylic acid halide, preferably the chloride, with benzyl alcohol to give pyridine-2,4- or -2,5-dicarboxylic acid benzyl ester; subsequent selective hydrolysis of the ester in the 2-position (for example in the presence of a copper catalyst, Loc.cit.Pharm. Acta Helv.), conversion of the free acid in the 2-position into the acid halide, reaction with a compound of the formula HX'—$R^{1'}$ (III) to give the pyridine-4- or -5-carboxylic acid benzyl ester-2-carboxylic acid ($R^1$) ester or -amide, hydrogenolytic splitting off of the benzyl protective group which remains (for example with $H_2$/Pt, see Houben-Weyl Volume IV/1c (1980), pages 381–82) and subsequent conversion of the free acid in the 4- or 5-position of the pyridine ring into the acid halide (IV).

The pyridine-2,4- or -2,5-dicarboxylic acid halide according to formula VI can be obtained by known methods, for example by reaction of pyridine-2,4- or -2,5-dicarboxylic acid with a phosphorus trihalide (see, for example, Organikum, Organisch Chemisches Grundpraktikum (Basic Practical Organic Chemistry), 15th edition, VEB Deutscher Verlag der Wissenschaften, 1976, pages 527 and 595 et seq.).

The reaction of alkali metal salts of the pyridine-2,4- or -2,5-dicarboxylic acid with a halide of the formula VIII is carried out by processes which are known from the literature (see, for example, Organikum, Organisch Chemisches Grundpraktikum (Basic Practical Organic Chemistry), 15th edition, VEB Deutscher Verlag der Wissenschaften, 1976, page 255 et seq.).

The compounds of the formula I and I' according to the invention have useful pharmacological properties, and in particular show an activity as inhibitors of proline hydroxylase and lysine hydroxylase and as fibrosuppressants and immunosuppressants.

The activity of the fibrogenase can be determined by radioimmunological assay of the N-terminal propeptide of collagen type III or the N- or C-terminal crosslinking domains of collagen type IV (7s-collagen or type IV collagen-$NC_1$) in the serum.

For this purpose, the hydroxyproline, procollagen III, peptide, 7s-collagen and type IV collagen-$NC_1$ concentrations in the liver of a) untreated rats (control)
b) rats to which carbon tetrachloride had been administered ($CCl_4$ control)
c) rats to which first $CCl_4$ and then a compound according to the invention had been administered were measured (this test method is described by Rouiller, C., Experimental toxic injury of the Liver; in The Liver, C. Rouiller, Volume 2, pages 335–476, New York, Academic Press, 1964), The pharmacological activity of the substances according to the invention has been investigated in a series of experiments (see Table 1). A clear inhibition of proline hydroxylase and lysine hydroxylase was thereby found.

TABLE 1

| Substance from Example | Dosage | Hydroxyproline μg/mg of liver | Procollagen III peptide ng/ml | 7s-collagen ng/ml | type IV collagen-$NC_1$ ng/ml |
|---|---|---|---|---|---|
| 4 | 2 × 25 mg | 0.482 | 37.2 | 121.4 | 100.8 |
| $CCl_4$ control | | 0.773 | 73.9 | 308.7 | 168.4 |
| control | | 0.289 | 11.1 | 22.8 | 23.5 |

The compounds of the formula I and I' can be used as medicaments in the form of pharmaceutical preparations which contain them, if appropriate together with tolerated pharmaceutical excipients. The compounds can be used as medicines, for example in the form of pharmaceutical preparations which contain these compounds as a mixture with a pharmaceutical organic or inorganic excipient suitable for enteral, percutaneous or parenteral administration, such as, for example, water, gum arabic, gelatin, lactose, starch, magnesium stearate, talc, vegetable oils, polyalkylene glycols, vaseline and the like.

The pharmaceutical preparations can be in the solid form, for example as tablets, coated tablets, suppositories or capsules; in the semi-solid form, for example as ointments, or in the liquid form, for example as solutions, suspensions or emulsions. If appropriate, they are sterilized and/or contain auxiliaries, such as preservatives, stabilizers, wetting agents or emulsifying agents, salts for modifying the osmotic pressure or buffers. They can furthermore also contain other therapeutically active substances.

The invention is illustrated in more detail with the aid of examples below:

EXAMPLES

1. Bis(1-methoxycarbonylethyl) pyridine-2,5-dicarboxylate 10 g of pyridine-2,5-dicarboxylic acid are taken in 60 ml of dry methylene chloride, and 80 ml of freshly distilled thionyl chloride and 2 ml of dry dimethylformamide are added. The mixture is boiled under reflux for three hours, the excess thionyl chloride and the methylene chloride are then distilled off and the residue is evaporated, with fuming, once with dry toluene. A solution of 12.5 g of methyl lactate, dissolved in methylene chloride, is added dropwise to the reaction mixture at −30° to −20° C. The mixture is allowed to warm slowly to room temperature and is stirred overnight at room temperature, and the solution is washed with sodium bicarbonate solution After drying, the organic phase is freed from the solvent and chromatographed over silica gel with ethyl acetate as the mobile phase. The product is recrystallized from isopropanol.

Melting point 78° C.; yield 7.2 g

2. Bis(1-ethoxycarbonylethyl) pyridine-2,5-dicarboxylate 10 g of pyridine-2,5-dicarboxylic acid are taken in 60 ml of dry methylene chloride, and 80 ml of freshly distilled thionyl chloride and 2 ml of dry dimethylformamide are added. The mixture is boiled under reflux for three hours, the excess thionyl chloride and the methylene chloride are distilled off and the residue is evaporated, with fuming, once with dry toluene. A solution of 14.1 g of ethyl lactate, dissolved in 1 l of methylene chloride, is added dropwise to the reaction mixture at −30° to −20° C. The mixture is allowed to warm slowly to room temperature and is stirred overnight at room temperature and the solution is washed with sodium bicarbonate solution. After drying, the organic phase is freed from the solvent and chromatographed over silica gel with ethyl acetate as the mobile phase. The product is precipitated as an oil.

Yield 16.6 g

3. Bis(1-isopropoxycarbonylethyl) pyridine-2,5-dicarboxylate 10 g of pyridine-2,5-dicarboxylic acid are taken in 60 ml of dry methylene chloride, and 80 ml of freshly distilled thionyl chloride and 2 ml of dry dimethylformamide are added. The mixture is boiled under reflux for three hours, the excess thionyl chloride and the methylene chloride are then distilled off and the residue is evaporated, with fuming, once with dry toluene. A solution of 15.8 g of isopropyl lactate, dissolved in 100 ml of methylene chloride, is added to the reaction mixture at −30° to −20° C. The mixture is allowed to warm slowly to room temperature and is stirred overnight at room temperature, and the solution is washed with sodium bicarbonate solution. After drying, the organic phase is freed from the solvent and stirred with diisopropyl ether. The monoester is separated off and the mother liquor is chromatographed over silica gel with a mixture of four parts of toluene and one part of ethyl acetate as the mobile phase. The oily product slowly crystallizes completely.

Melting point 52°–53° C. Yield 13.5 g

4. Bis(2-methoxycarbonyl-2,2-dimethylethyl) pyridine-2,5-dicarboxylate 10 g of pyridine-2,5-dicarboxylic acid are taken in 60 ml of dry methylene chloride, and 80 ml of freshly distilled thionyl chloride and 2 ml of dry dimethylformamide are added. The mixture is boiled under reflux for three hours, the excess thionyl chloride and the methylene chloride are then distilled off and the residue is evaporated, with fuming, once with dry toluene. A solution of 15.8 g of methyl 2,2-dimethyl-3-hydroxypropionate, dissolved in 100 ml of methylene chloride, is added to the reaction mixture at −30° to −20° C. The mixture is allowed to warm slowly to room temperature and is stirred overnight at room temperature and the solution is washed with sodium bicarbonate solution.

After drying, the organic phase is freed from the solvent and the product is recrystallized from isopropanol.

Melting point 114°–5° C. Yield 18.6 g

5. Bis(2-methoxycarbonyl-2,2-dimethylethyl) pyridine-2,4-dicarboxylate 7.5 g of pyridine-2,5-dicarboxylic acid are taken in 45 ml of dry methylene chloride, and 60 ml of freshly distilled thionyl chloride and 2 ml of dry dimethylformamide are added. The mixture is boiled under reflux for three hours, the excess thionyl chloride and the methylene chloride are then distilled off and the residue is evaporated, with fuming, once with dry toluene. A solution of 11.9 g of methyl 2,2-dimethyl-3-hydroxypropionate, dissolved in 100 ml of methylene chloride, is added to the reaction mixture at −30° to −20° C. The mixture is allowed to warm slowly to room temperature and is stirred overnight at room temperature and the solution is washed with sodium bicarbonate solution.

After drying, the organic phase is freed from the solvent and chromatographed over silica gel with ethyl acetate as the mobile phase. The product is obtained as an oil.

Yield 6.7 g.

6. Bis(1-ethoxycarbonylethyl) pyridine-2,4-dicarboxylate 7.5 g of pyridine-2,4-dicarboxylic acid are taken in 45 ml of dry methylene chloride, and 60 ml of freshly distilled thionyl chloride and 2 ml of dry dimethylformamide are added. The mixture is boiled for three hours, the excess thionyl chloride and the methylene chloride are then distilled off and the residue is evaporated, with fuming, once with dry toluene. A solution of 10.6 g of ethyl lactate, dissolved in 100 ml of methylene chloride, is added dropwise to the reaction mixture at −30° to −20° C. The mixture is allowed to warm slowly to room temperature and is stirred overnight at room temperature and the solution is washed with sodium bicarbonate solution. After drying, the organic phase is freed from the solvent and chromatographed over silica gel with ethyl acetate as the mobile phase. The product is obtained as an oil, which slowly crystallizes completely.

Melting point 59°–60° C. Yield 3.7 g.

7. Bis(5-methyl-2-oxo-1,3-dioxol-4-ylmethyl) pyridine-2,4-dicarboxylate 6.3 g of-pyridine-2,4-dicarboxylic acid sodium salt are boiled under reflux with 14.3 g of 5-methyl-2-oxo-1,3-dioxol-4-yl-methyl bromide and 4.5 g of potassium carbonate in 125 ml of dry acetone for 40 hours. The carbonate is filtered off and the solution is chromatographed over silica gel with a 4:1 mixture of toluene and ethyl acetate.

Melting point 113° C. Yield 2.6 g

8. Methyl 2-(4-(2-phenylethyl)piperazinocarbonyl)-pyridine-5-carboxylate 1.5 g of methyl pyridine-2-(carboxylic acid)-5-carboxylate are heated under reflux with 22.5 ml of freshly distilled thionyl chloride until a clear solution has formed. The solution is subsequently stirred at room temperature for one hour and the thionyl chloride is distilled off completely. The residue is taken up in 15 ml of dry methylene chloride, the mixture is added to a solution of 3.15 g of 1-(2-phenylethyl)-piperazine in 8 ml of methylene chloride and the components are subsequently stirred at room temperature for five minutes and freed from the solvent. The residue is recrystallized from isopropanol, with the addition of a little active charcoal. The product is obtained as the hydrochloride.

Melting point 201°–203° C. Yield 2.6 g

9. Methyl 2-benzylaminocarbonyl-pyridine-5-carboxylate 1.5 g of methyl pyridine-2-(carboxylic acid)-5-carboxylate are heated under reflux with 22.5 ml of freshly distilled thionyl chloride until a clear solution has formed. The solution is subsequently stirred at room temperature for one hour and the thionyl chloride is distilled off completely. The residue is taken up in 15 ml of dry methylene chloride, the mixture is added dropwise to 8 solution of 1.15 g of benzylamine in 8 ml of methylene chloride and the components are subsequently stirred at room temperature for five minutes and freed from the solvent. The residue is recrystallized from isopropanol, with the addition of a little active charcoal.

Melting point 215°–216° C. Yield 1.9 g

10. Methyl 2-(N-benzyl-N-methylaminocarbonyl)-pyridine-5-carboxylate 1.5 g of methyl pyridine-2-(carboxylic acid)-5-carboxylate are heated under reflux with 22.5 ml of freshly distilled thionyl chloride until a clear solution has formed. The solution is subsequently stirred at room temperature for one hour and the thionyl chloride is distilled off completely. The residue is taken up in 15 ml of dry methylene chloride, the mixture is added dropwise to a solution of 2.0 g of N-methylbenzylamine in 8 ml of methylene chloride and the components are subsequently stirred at room temperature for five minutes and freed from the solvent. The residue is chromatographed over silica get with a mixture of 7 parts of methylene chloride and 3 parts of acetone.

The product is obtained as an oil.

11. Methyl 2-benzyloxycarbonylpyridine-5-carboxylate 1.5 g of methyl pyridine-2-(carboxylic acid)-5-carboxylate are heated under reflux with 22.5 ml of freshly distilled thionyl chloride until a clear solution has formed, The solution is subsequently stirred at room temperature for one hour and the thionyl chloride is distilled off completely. The residue is taken up in 15 ml of dry methylene chloride, the mixture is added dropwise to a solution of 1.79 g of benzylalcohol in 8 ml of methylene chloride and the components are subsequently stirred at room temperature for five minutes and freed from the solvent, The residue is recrystallized from isopropanol, with the addition of a little active charcoal.

Melting point 104° C. Yield 1.5 g

12. Methyl 2-phenylaminocarbonylpyridine-5-carboxylate 1.5 g of methyl pyridine-2-(carboxylic acid)-5-carboxylate are heated under reflux with 22.5 ml of freshly distilled thionyl chloride until a clear solution has formed, The solution is subsequently stirred at room temperature for one hour and the thionyl chloride is distilled off completely, The residue is taken up in 15 ml of dry methylene chloride, the mixture is added dropwise to a solution of 1.54 g of aniline in 8 ml of methylene chloride and the components are subsequently stirred at room temperature for five minutes and freed from the solvent, The residue is recrystallized from isopropanol, with the addition of a little active charcoal.

Melting point 167° C. Yield 1.5 g

13. Methyl 2-(2,2-diphenylethylamino)carbonylpyridine-5-carboxylate 1.5 g of methyl pyridine-2-(carboxylic acid)-5-carboxylate are heated under reflux with 22.5 ml of freshly distilled thionyl chloride until a clear solution has formed. The solution is subsequently stirred at room temperature for one hour and the thionyl chloride is distilled off completely. The residue is taken up in 15 ml of dry methylene chloride, the mixture is added dropwise to a solution of 3.27 g of diphenylethylamine in 8 ml of methylene chloride and the components are subsequently stirred at room temperature for five minutes and freed from the solvent. The residue is recrystallized from isopropanol, with the addition of a little active charcoal.

Melting point 147° C. Yield 1.8 g

14. Methyl 2-(N-methyl-N-phenylamino)carbonylpyridine-5-carboxylate 25.5 g of methyl pyridine-2-(carboxylic acid)-5-carboxylate are heated under reflux with 380 ml of freshly distilled thionyl chloride until a clear solution has formed. The solution is subsequently stirred at room temperature for one hour and the thionyl chloride is distilled off completely. The residue is taken up in 250 ml of dry methylene chloride, the mixture is added dropwise to a solution of 30 g of N-methylaniline in 150 ml of methylenechloride and the components are subsequently stirred at room temperature for five minutes and freed from the solvent. The residue is recrystallized from isopropanol, with the addition of a little active charcoal.

Melting point 123° C. Yield 30 g

15. Methyl 2-N-propylamino-carbonylpyridine-5-carboxylate 15 g of methyl pyridine-2-(carboxylic acid)-5-carboxylate are heated under reflux with 225 ml of freshly distilled thionyl chloride until a clear solution has formed. The solution is subsequently stirred at room temperature for one hour and the thionyl chloride is distilled off completely. The residue is taken up in 70 ml of dry methylene chloride, the mixture is added dropwise to a solution of 13.7 g of propylamine in 150 ml of methylene chloride and the components are subsequently stirred at room temperature for five minutes and freed from the solvent. The residue is chromatographed over silica gel with a mixture of 7 parts of methylene chloride and 3 parts of acetone as the mobile phase.

Melting point 88° C. Yield 12.6 g

16. Di(4-nitro-phenyl) pyridine-2,5-dicarboxylate 16.7 g of pyridine-2,5-dicarboxylic acid are taken in 100 ml of dry methylene chloride, and 135 ml of freshly distilled thionyl chloride and 3 ml of dry dimethylformamide are added. The mixture is boiled under reflux for three hours, the excess thionyl chloride and the methylene chloride are then distilled off and the residue is evaporated, with fuming, once with dry toluene. A solution of 27.8 g of 4-nitrophenol in 50 ml of pyridine is added dropwise to the reaction mixture at −30° to −20° C. The mixture is allowed to warm slowly to room temperature and is stirred overnight at room temperature and the solution is washed with sodium bicarbonate solution. After drying, the organic phase is freed from the solvent and chromatographed over silica gel with ethyl acetate as the mobile phase.

Melting point 190° C. Yield 12.5 g

17. Bis(5-methyl-2-oxo-1,3-dioxol-4-yl-methyl) pyridine-2,5-dicarboxylate

Analogously to Example 7, 6.3 g of pyridine-2,5-dicarboxylic acid sodium salt are reacted with 14.3 g of 5-methyl-2-oxo-1,3-dioxol-4-yl-methyl bromide and the mixture is boiled under reflux in acetone for 2.5 hours. After chromatography over silica gel with ethyl acetate as the mobile phase, the product is recrystallized from hot ethyl acetate.

Melting point 118° C. Yield 0.23 g

18. Di-(α-methoxycarbonylbenzyl) pyridine-2,5-dicarboxylate

Analogously to Example 1, 10 g of pyridine-2,5-dicarboxylic acid are converted into the acid chloride and this is reacted with 19.9 g of methyl (±)-mandelate. After extraction, working up is carried out by chromatography over silica gel with a mixture of toluene and ethyl acetate as the mobile phase.

Melting point 125° C. Yield 0.5 g

19. Methyl pyridine-2-carboxamide-5-carboxylate 20 g of methyl pyridine-2-(carboxylic acid)-5-carboxylate are converted into the acid chloride with 200 g of thionyl chloride as described in Example 8. The acid chloride is dissolved in chloroform, and ammonia gas is passed over the suspension, with vigorous stirring, The mixture is left to stand for two days and the product is filtered off with suction and washed with water.

Melting point 195°–197° C. Yield 15.6 g

20. Dibenzyl pyridine-2,5-dicarboxylate

Analogously to Example 1, 20 g of pyridine-2,5-dicarboxylic acid are converted into the acid chloride with 160 ml of thionyl chloride and this is reacted with 25.9 g of benzyl alcohol. The product is recrystallized from ethyl acetate, with the addition of active charcoal.

Melting point 110° C. Yield 20.4 g

21. Benzyl pyridine-2-(carboxylic acid)-5-carboxylate 17 g of dibenzyl pyridine-2,5-dicarboxylate are suspended in methanol and the suspension is added to a suspension of 12.1 g of copper(II) nitrate. The mixture is boiled under reflux for one hour and, after cooling, the copper complex is filtered off. The complex is suspended in dioxane, and hydrogen sulfide is passed in up to a weight increase of 4 g. The copper sulfide is separated off and the organic phase is concentrated. The product is recrystallized from toluene.

Melting point 132° C. Yield 10.2 g

22. Benzyl pyridine-2-(3-isopropoxy-propyl)carboxamide-5-carboxylate

Analogously to Example 8, 8 g of 5-benzyl pyridine-2-carboxylate are converted into the acid chloride with 90 ml of thionyl chloride and this is reacted with 3-isopropoxy-propylamine to give the amide. For purification, the product is chromatographed over silica gel with a mixture of cyclohexane/ethyl acetate (1:1).

Melting point 41° C. Yield 6.4 g

23. Pyridine-5-carboxylic acid 2-(3-isopropoxy-propyl)carboxamide 5.3 g of benzyl pyridine-2-(3-isopropoxy-propyl)carboxamide-5-carboxylate are hydrogenated in dioxane under normal pressure in the presence of a palladium-on-charcoal catalyst for five hours. When the uptake of hydrogen has ended, the catalyst is filtered off with suction and the solvent is stripped off.

Melting point 129° C. Yield 2.4 g

24. Benzyl pyridine-2-(3-isopropoxy-propyl)carboxamide-5-carboxylate

In accordance with Example 8, 1 g of pyridine-5-carboxylic acid 2-(3-isopropoxy-propyl)amide are converted into the acid chloride (20 ml of thionyl chloride) and this is then reacted with 2 ml of benzyl alcohol to give benzyl pyridine-2-(isopropoxypropyl)carboxamide-5-carboxylate. For purification, the product is chromatographed over silica gel with a mixture of cyclohexane/ethyl acetate (1:1).

Melting point 41° C. Yield 0.9 g

25. Di(5-methyl-2-nitro-benzyl) pyridine-2,5-dicarboxylate

Analogously to Example 1, 5 g of pyridine-2,5-dicarboxylic acid are converted into the acid chloride with 40 ml of thionyl chloride in 30 ml of methylene chloride and this is reacted with 10 g of 5-methyl-2-nitro-benzyl alcohol in 50 ml of methylene chloride. The reaction mixture is stirred overnight at room temperature, sodium bicarbonate solution is then added, the mixture is extracted with methylene chloride and the organic phase is dried, After the solvent has been stripped off, the residue is stirred with ethyl acetate, filtered off with suction and recrystallized twice from methylene chloride.

Melting point 182° C. Yield 2.9 g

26. Bis(2-ethoxy-ethyl) pyridine-2,5-dicarboxylate

Analogously to Example 1, 10 g of pyridine-2,5-dicarboxylic acid are converted into the acid chloride with 80 ml of thionyl chloride in 60 ml of methylene chloride and this is reacted with 10.78 g of ethylene glycol monomethyl ether in 100 ml of methylene chloride. Working up is by adding sodium bicarbonate solution, separating off the organic phase and stripping off the solvent. The product is chromatographed twice over silica gel with ethyl acetate and dissolved in hot ethyl acetate, and the solution is clarified with active charcoal and freed from the solvent. The product precipitates as an oil.

Yield 7.2 g

27. Bis(2-methoxy-ethyl) pyridine-2,5-dicarboxylate

Analogously to Example 26, 10 g of pyridine-2,5-dicarboxylic acid are converted into the acid chloride and this is reacted with 9.1 g of ethylene glycol monomethyl ether. Working up is carried out in accordance with Example 26. The product is obtained as an oil.

Yield 6.5 g

28. Bis(2-ethoxy-ethyl) pyridine-2,4-dicarboxylate

As described in Example 26, 10 g of pyridine-2,4-dicarboxylic acid are reacted with ethylene glycol monoethyl ether via the acid chloride. The reaction

29. 2-Methoxycarbonyl-2-methyl-propyl pyridine-5-carboxylate-2-N-(3-isopropoxy-propyl)carboxamide 1 g of pyridine-5-carboxylic acid 2-(3-isopropoxy-propyl)carboxamide are boiled under reflux in 20 ml of thionyl chloride until a solution is obtained. The solution is left to stand at room temperature for one hour, the thionyl chloride is distilled off, the residue is dissolved in 10 ml of dry methylene chloride and a solution of 0.5 g of methyl 2,2-dimethyl-3-hydroxypropionate 20 ml of dry methylene chloride is added dropwise. When the reaction has ended, the solvent is stripped off and the product is chromatographed over silica gel with ethyl acetate.

Yield 0.15 g

30. Bis(1-isopropoxycarbonylethyl) pyridine-2,4-dicarboxylate 10 g of pyridine-2,4-dicarboxylic acid are taken in 60 ml of dry methylene chloride, and 80 ml of freshly distilled thionyl chloride and 2 ml of dry dimethylformamide are added. The mixture is boiled under reflux for three hours, the excess thionyl chloride and the methylene chloride are then distilled off and the residue is evaporated, with fuming, once with dry toluene, A solution of 15.8 g of isopropyl lactate dissolved in 100 ml of methylene chloride, is added dropwise to the reaction mixture at $-30°$ to $-20°$ C. The mixture is allowed to warm slowly to room temperature and is stirred overnight at room temperature and the solution is washed with sodium bicarbonate solution, After drying, the organic phase is freed from the solvent and stirred with diisopropyl ether. The monoester is separated off and the mother liquor is chromatographed over silica gel with a mixture of four parts of toluene and one part of ethyl acetate as the mobile phase. The product is obtained as an oil.

Yield: 11.2 g

We claim:

1. A pharmaceutical composition comprising an amount effective for use in the therapy of a mammal of a compound of the formula I

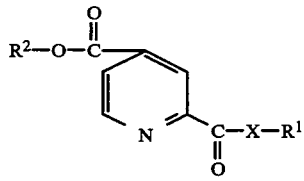

in which
R$^1$ denotes branched or unbranched C$_1$–C$_{12}$-alkyl which is optionally monosubstituted or, in the case of the C$_2$–C$_{12}$-alkyl radicals, also polysubstituted by halogen, hydroxyl, cyano, carboxyl, alkoxy, alkoxycarbonyl, alkylcarbonyloxy, alkyl- or dialkylamino, the alkyl radicals containing 1–4 carbon atoms and, in the case of the C$_3$- and C$_4$-alkyl radicals, it also being possible for them to be branched, phenyl, which is in turn optionally mono-, di- or trisubstituted by halogen, nitro, C$_1$–C$_4$-alkyl or C$_1$–C$_4$-alkoxy, it also being possible, in the case of polysubstitution, for the substituents to differ independently of one another and it also being possible, in the case of the C$_3$- and C$_4$-alkyl radicals, for these to be branched, or R$^1$ denotes saturated C$_5$–C$_7$-cycloalkyl, which is optionally benzo-fused, or R$^1$ denotes aryl or heteroaryl, which in turn is optionally mono-, di- or trisubstituted by halogen, nitro, C$_1$–C$_4$-alkyl or C$_1$–C$_4$-alkoxy, it also being possible, in the case of polysubstitution, for the substituents to differ independently of one another and it also being possible, in the case of the C$_3$- and C$_4$-alkyl radicals, for these to be branched, or R$^1$ denotes 2-oxo-1,3-dioxolylmethyl, which is optionally also methyl-substituted, or R$^1$ denotes hydrogen, and R$^2$ independently of R$^1$ denotes hydrogen or is selected from the values of R$^1$ and X denotes R$^3$-substituted nitrogen, in which R$^3$ is hydrogen or C$_1$–C$_6$-alkyl or, together with R$^1$, optionally forms a heterocyclic saturated 5-, 6- or 7-ring, it also being possible for the heterocyclic ring to include a second nitrogen atom and it being possible for the heterocyclic ring in turn to be substituted by phenyl or phenyl-C$_1$–C$_3$-alkyl, or a physiologically tolerated salt thereof, together with a pharmaceutically acceptable carrier.

2. A pharmaceutical composition comprising an amount effective for use in the therapy of a mammal of a compound of the formula I

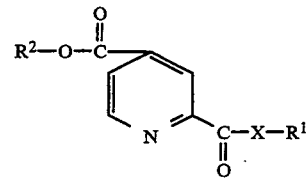

in which
R$^1$ denotes branched or unbranched C$_1$–C$_4$-alkyl which is optionally monosubstituted or, in the case of the C$_3$- and C$_4$-alkyl radicals, also polysubstituted by C$_1$–C$_3$-alkoxy and/or C$_1$–C$_3$-alkoxycarbonyl, it also being possible for the C$_3$-alkyl radicals to be branched, and/or phenyl, or R$^1$ denotes C$_5$- or C$_6$-cycloalkyl, which is optionally benzo-fused, or R$^1$ denotes phenyl, which is optionally mono-, di- or trisubstituted by nitro, or R$^1$ denotes 2-, 3- or 4-pyridyl, naphthyl, 2- or 3-thienyl, pyrazolyl, imidazolyl or thiazolyl, or R$^1$ denotes 5-methyl-2-oxo-1,3-dioxol-4-yl-methyl and R$^2$ independently of R$^1$ denotes hydrogen or is selected from the values of R$^1$, and X denotes R$^3$-substituted nitrogen, in which R$^3$ is hydrogen or C$_1$–C$_3$-alkyl or, together with R$^1$, optionally forms a heterocyclic saturated 6-ring, it also being possible for the heterocyclic 6-ring to include a second nitrogen atom and to be substituted in turn by phenyl or phenyl-C$_1$–C$_3$-alkyl, or a physiologically tolerated salt thereof, together with a pharmaceutically acceptable carrier.

3. A compound of the formula I'

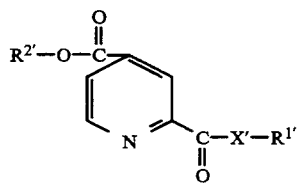

in which

R$^{1'}$ denotes branched or unbranched C$_1$–C$_{12}$-alkyl which is optionally monosubstituted or, in the case of C$_2$–C$_{12}$-alkyl, also polysubstituted by halogen, hydroxyl, cyano, carboxyl, alkoxy, alkoxycarbonyl, alkylcarbonyloxy, alkyl- or dialkylamino, the alkyl radicals containing 1–4 carbon atoms and it also being possible, in the case of the C$_3$- and C$_4$-alkyl radicals, for these to be branched, phenyl, which is in turn optionally mono-, di- or trisubstituted by halogen, nitro, C$_1$–C$_4$-alkoxy or C$_1$–C$_4$-alkyl, it also being possible for the C$_3$- and C$_4$-alkyl radicals mentioned to be branched and it also being possible, in the case of polysubstitution, for the substituents to differ independently of one another, or R$^{1'}$ denotes saturated C$_5$–C$_7$-cycloalkyl, which is optionally benzo-fused, or R$^{1'}$ denotes aryl or heteroaryl, which is in turn optionally mono-, di- or trisubstituted by halogen, nitro, C$_1$–C$_4$-alkyl or C$_1$–C$_4$-alkoxy, it also being possible, in the case of polysubstitution, for the substituents to differ independently of one another and it also being possible, in the case of the C$_3$- and C$_4$-alkyl radicals, for these to be branched, or R$^{1'}$ denotes 2-oxo-1,3-dioxolylmethyl, which is optionally methyl-substituted, or R$^{1'}$ denotes hydrogen, and R$^{2'}$ independently of R$^{1'}$ denotes hydrogen or is selected from the values of R$^{1'}$ and X' denotes R$^{3'}$-substituted nitrogen, in which R$^{3'}$ is hydrogen or C$_1$–C$_6$-alkyl or, together with R$^{1'}$, optionally forms a heterocyclic, saturated 5-, 6- or 7-ring, it also being possible for the heterocyclic ring to include a second nitrogen atom and it being possible for the heterocyclic ring in turn to be substituted by phenyl or phenyl-C$_1$–C$_3$-alkyl, or a physiologically tolerated salt thereof, excluding the compounds in which R$^{1'}$ and R$^{3'}$ are hydrogen and R$^{2'}$ is hydrogen or methyl.

4. A compound as claimed in claim 3, in which

R$^{1'}$ denotes branched or unbranched C$_1$–C$_4$-alkyl, which is optionally monosubstituted or, in the case of the C$_2$–C$_4$-alkyl radicals, also polysubstituted by alkoxy or alkoxycarbonyl, the alkyl radicals containing 1–3 carbon atoms and it also being possible, in the case of the C$_3$-alkyl compounds, for these to be branched, or phenyl, or R$^{1'}$ denotes cyclopentyl or cyclohexyl, which are optionally benzo-fused, or R$^{1'}$ denotes phenyl, which is optionally substituted by 1, 2 or 3 nitro groups, or naphthyl, or R$^{1'}$ denotes 2-, 3- or 4-pyridyl, 3-thienyl, pyrazolyl, imidazolyl or thiazolyl, or R$^{1'}$ denotes 5-methyl-2-oxo-1,3-dioxol-4-yl-methyl and R$^{2'}$ independently of R$^{1'}$ denotes hydrogen or one of the foregoing values of R$^{1'}$, and X' denotes R$^{3'}$-substituted nitrogen, in which R$^{3'}$ is hydrogen or C$_1$–C$_3$-alkyl or together with R$^{1'}$, optionally forms a heterocyclic, saturated 6-ring, it also being possible for the heterocyclic 6-ring to include a second nitrogen atom and in turn to be substituted by phenyl or phenyl-C$_1$–C$_3$-alkyl, or a physiologically tolerated salt thereof.

5. A method for inhibiting proline hydroxylase and lysine hydroxylase in a mammal which comprises administering an effective amount of a compound as claimed in claim 3.

6. A method for treating a mammal with a fibrosuppressant or immunosuppressant which comprises administering an effective amount of a compound as claimed in claim 3.

7. A method for treatment of disturbances in the metabolism of collagen and collagen-like substances or the biosynthesis of C1$_q$ in a mammal which comprises administering an effective amount of a compound as claimed in claim 3.

8. A method for influencing the metabolism of collagen and collagen-like substances or the biosynthesis of C1$_q$ in a mammal which comprises administering an effective amount of a compound as claimed in claim 3.

9. A method for inhibiting proline hydroxylase and lysine hydroxylase in a mammal which comprises administering an effective amount of a pharmaceutical composition as claimed in claim 1.

10. A method for treating a mammal with a fibrosuppressant or immunosuppressant which comprises administering an effective amount of a pharmaceutical composition as claimed in claim 1.

11. A method for treatment of disturbances in the metabolism of collagen and collagen-like substances or the biosynthesis of C1$_q$ in a mammal which comprises administering an effective amount of a pharmaceutical composition as claimed in claim 1.

12. A method for influencing the metabolism of collagen and collagen-like substances or the biosynthesis of C1$_q$ in a mammal which comprises administering an effective amount of a pharmaceutical composition as claimed in claim 1.

* * * * *

UNITED STATES PATENT AND TRADEMARK OFFICE
CERTIFICATE OF CORRECTION

PATENT NO. : 5,364,873
DATED : November 15, 1994
INVENTOR(S) : Martin BICKEL et al.

It is certified that error appears in the above-indentified patent and that said Letters Patent is hereby corrected as shown below:

In the title , On title page, Item [54], Line 3, "COMPOSITION" should read --COMPOSITIONS--.

Inventors, Title Page, Item [75], Line 5, after "Taunus" and before the comma (,) insert --;Hartmut Hanauske-Abel, Dexheim--.

Claim 4, Column 18, Line 14, after "or" insert --,--.

Signed and Sealed this

Sixth Day of August, 1996

Attest:

BRUCE LEHMAN

*Attesting Officer*   Commissioner of Patents and Trademarks